US009568476B2

(12) United States Patent
Hayes

(10) Patent No.: US 9,568,476 B2
(45) Date of Patent: *Feb. 14, 2017

(54) DIAGNOSIS AND TREATMENT OF BREAST CANCER

(71) Applicant: The Regents of The University of Michigan, Ann Arbor, MI (US)

(72) Inventor: Daniel Hayes, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/304,364

(22) Filed: Jun. 13, 2014

(65) Prior Publication Data

US 2014/0295444 A1 Oct. 2, 2014

Related U.S. Application Data

(63) Continuation of application No. 13/178,128, filed on Jul. 7, 2011, now Pat. No. 8,790,878.

(60) Provisional application No. 61/469,890, filed on Mar. 31, 2011, provisional application No. 61/362,021, filed on Jul. 7, 2010.

(51) Int. Cl.
| | | |
|---|---|---|
| *C12Q 1/68* | (2006.01) | |
| *G01N 33/574* | (2006.01) | |
| *G01N 33/50* | (2006.01) | |
| *G01N 33/566* | (2006.01) | |
| *G01N 33/577* | (2006.01) | |

(52) U.S. Cl.
CPC ......... *G01N 33/57415* (2013.01); *C12Q 1/686* (2013.01); *C12Q 1/6886* (2013.01); *G01N 33/5091* (2013.01); *G01N 33/566* (2013.01); *G01N 33/577* (2013.01); *C12Q 2600/106* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 2002/0172987 A1* | 11/2002 | Terstappen et al. | 435/7.23 |
| 2005/0079557 A1 | 4/2005 | Vendrell | |
| 2005/0181463 A1* | 8/2005 | Rao et al. | 435/7.23 |
| 2007/0037173 A1 | 2/2007 | Allard et al. | |
| 2007/0231822 A1 | 10/2007 | Mitas et al. | |
| 2008/0038725 A1 | 2/2008 | Luo et al. | |
| 2008/0113350 A1 | 5/2008 | Terstappen | |
| 2009/0118175 A1 | 5/2009 | Macina | |
| 2010/0311601 A1* | 12/2010 | Symmans et al. | 506/8 |

FOREIGN PATENT DOCUMENTS

| | | |
|---|---|---|
| WO | 03065042 A1 | 8/2003 |
| WO | 2004027418 | 4/2004 |
| WO | 2004076643 A2 | 9/2004 |
| WO | 2007035842 A2 | 3/2007 |
| WO | 2008145125 | 12/2008 |
| WO | 2009108637 A1 | 9/2009 |

OTHER PUBLICATIONS

Miller et al. (Significance of Circulating Tumor Cells Detected by the CellSearch System in Patients with Metastatic Breast Colorectal and Prostate Cancer, Journal of Oncology vol. 2010 (2010), Article ID 617421, 8 pages).*
Johnston et al. (New Strategies in Estrogen Receptor-Positive Breast Cancer, Clin Cancer Res. Apr. 1, 2010;16(7):1979-87, Epub Mar. 23, 2010).*
Arpino et al. (Crosstalk between the Estrogen Receptor and the HER Tyrosine Kinase Receptor Family: Molecular Mechanism and Clinical Implications for Endocrine Therapy Resistance, Endocr Rev. Apr. 2008;29(2):217-33. Epub Jan. 23, 2008).*
Wulfing et al. (HER2-Positive Circulating Tumor Cells Indicate Poor Clinical Outcome in Stage I to III Breast Cancer Patients, Clin Cancer Res. Mar. 15, 2006;12(6):1715-20).*
Fehm et al. (Presence of apoptotic and nonapoptotic disseminated tumor cells reflects the response to neoadjuvant systemic therapy in breast cancer, Breast Cancer Res. 2006;8(5):R60, Published: Oct. 24, 2006).*
Allan et al. (Circulating Tumor Cell Analysis: Technical and Statistical Considerations for Application to the Clinic, J Oncol. 2010;2010:426218. Epub Dec. 13, 2009).*
Meng et al. (HER-2 gene amplification can be acquired as breast cancer progresses, Proc Natl Acad Sci U S A. Jun. 22, 2004;101(25):9393-8. Epub Jun. 11, 2004).*
Ignatiadis et al. (Circulating Tumor Cells in Breast Cancer, in Breast Cancer Risk Reduction and Early Detection, Ch. 13, pp. 219-234, eds. E.R. Sauter, M.B. Daly, Aug. 2009).*
Nakagawa et al. (Detection of Circulating Tumor Cells in Early-Stage Breast Cancer Metastasis to Axillary Lymph Nodes, Clin Cancer Res. Jul. 15, 2007;13(14):4105-10).*
Pachmann et al. (Monitoring the Response of Circulating Epithelial Tumor Cells to Adjuvant Chemotherapy in Breast Cancer Allows Detection of Patients at Risk of Early Relapse, J Clin Oncol. Mar. 10, 2008;26(8):1208-15).*
Muller et al. (Circulating Tumor Cells in Breast Cancer: Correlation to Bone Marrow Micrometastases, Heterogeneous Response to Systemic Therapy and Low Proliferative Activity, Clin Cancer Res. May 15, 2005;11(10):3678-85).*

(Continued)

*Primary Examiner* — Aaron Priest
(74) *Attorney, Agent, or Firm* — Casimir Jones, S.C.

(57) ABSTRACT

The present invention relates to compositions and methods for cancer diagnosis, research and therapy, including but not limited to, cancer markers. In particular, the present invention relates to compositions and methods for the prediction of a subject's response to cancer therapies.

17 Claims, 11 Drawing Sheets

(56) References Cited

OTHER PUBLICATIONS

Dikicioglu et al. (Biological characteristics of breast cancer at the primary tumour and the involved lymph nodes, Int J Clin Pract. Sep. 2005;59(9):1039-44).*
Mamounas et al. (The Oncotype DX Breast Cancer Assay—An Expert Q&A and Case Study Sampling, Clinical Advances in Hematology & Oncology vol. 6, Issue 2, Supplement Feb. 3, 2008).*
Neubauer et al. (Changes in Tumour Biological Markers during Primary Systemic Chemotherapy (PST), Anticancer Res. May-Jun. 2008;28(3B):1797-804).*
Faneyte et al. (Breast cancer response to neoadjuvant chemotherapy: predictive markers and relation with outcome, Br J Cancer. Feb. 10, 2003;88(3):406-12).*
Aas et al. (Predictive value of tumour cell proliferation in locally advanced breast cancer treated with neoadjuvant chemotherapy, Eur J Cancer. Mar. 2003;39(4):438-46).*
Oakman et al. (New diagnostics and biological predictors of outcome in early breast cancer, Breast Cancer Res. 2009;11(2):205. Epub Apr. 3, 2009).*
Tonini et al. (Molecular prognostic factors: clinical implications in patients with breast cancer, Cancer Therapy vol. 6, 773-782, Dec. 2008).*
Meche et al. (Immunohistochemical expression and significance of epidermal growth factor receptor (EGFR) in breast cancer, Rom J Morphol Embryol. 2009;50(2):217-21).*
Cobleigh et al. (Tumor Gene Expression and Prognosis in Breast Cancer Patients with 10 or More Positive Lymph Nodes, Clin Cancer Res Dec. 15, 2005 11; 8623).*
Allard et al., "Tumor cells circulate in the peripheral blood of all major carcinomas but not in healthy subjects or patients with nonmalignant diseases." Clin Cancer Res. Oct. 15, 2004; 10(20):6897-904.
Anonymous: "High CTC Levels Predicted Poor Outcome in Metastatic Breast Cancer." Dec. 12, 2010, www.aacr.org.
Bastarrachea et al. "Obesity as an adverse prognostic factor for patients receiving adjuvant chemotherapy for breast cancer." Ann Intern Med. Jan. 1994, 120(1):18-25.
Budd et al., "Circulating Tumor Cells versus Imaging—Predicting Overall Survival in Metastatic Breast Cancer." Clinical Cancer Research, Nov. 1, 2006, 12(21):6403-6409.
Cristofanilli et al., "Circulating tumor cells, disease progression, and survival in metastatic breast cancer." N. Engl J Med. Aug. 19, 2004; 351(8):781-91.
Cristofanilli et al., "Circulating tumor cells: a novel prognostic factor for newly diagnosed metastatic breast cancer." J Clin Oncol. Mar. 1, 2005; 23(7):1420-30.
Edwards et al. "Infiltrating ductal carcinoma of the breast: the survival impact of race." J Clin Oncol. Aug. 1998, 16 (8): 2693-9.
Elledge et al., "Tumor biologic factors and breast cancer prognosis among white, Hispanic, and black women in the United States." J Natl Cancer Inst. May 1994;86(9):705-12.
Endo et al., "High Estrogen receptor expression and low K167 expression are associated with improved time to progression during first-line endocrine therapy with aromatase inhibitors in breast cancer." International Journal of Clinical Oncology, Mar. 23, 2011, 16(5): 512-518.
Fehm et al., "HER2 status of circulating tumor cells in patients with metastatic breast cancer: a prospective, multicenter trial." Breast Cancer Research and Treatment, Sep. 22, 2010, 124(2):403-412.
Gradilone et al., "Circulating tumor cells (CTCs) in metastic breast cancer (MBC): prognosis, drug resistance and phenotypic characterization." Annals of Oncology Jan. 1, 2011, 22(1):86-92.
Hayes et al., "Tumor Marker Utility Grading System: A Framework to Evaluate Clinical Untility of Tumor Markers." JNCI Journal of the National Cancer Institute Oct. 16, 1996, 88(20): 1456-1466.
Hayes, "Circulating Tumor Cells at Each Follow-up Time Point during Therapy of Metastatic Breast Cancer Patients Predict Progression-Free and Overall Survival." Clinical Cancer Research, Jul. 15, 2006, 12(4): 4218-4224.
Liu et al., "Circulating tumor cells: a useful predictor of treatment efficacy in metastatic breast cancer." J Clin Oncol. Nov. 1, 2009; 27(31):5153-9.
Ma et al., "Predicting endocrine therapy responsiveness in breast cancer." Oncology Feb. 18, 2009, 23(2): 133-142.
Nabholtz et al, "Comparative review of anastrozole, letrozole and exemestane in the management of early breast cancer." Expert Opinion on Phamacology Jun. 1, 2009, 10(9): 1435-1447.
Paik et al., "A multigene assay to predict recurrence of tamoxifen-treated, node-negative breast cancer." N Engl J Med. Dec. 30, 2004;351(27):2817-26.
Paik et al., "Gene expression and benefit of chemotherapy in women with node-negative, estrogen receptor-positive breast cancer." J Clin Oncol. Aug. 10, 2006; 24(23):3726-34.
Pierga et al. "High independent prognostic and predictive value of circulating tumor cells compared with serum tumor markers in a large prospective trial in first-line chemotherapy for metastatic breast cancer patients." Ann Oncol. Mar. 2012; 23(3):618-24.
Pierga et al. "Circulating tumor cell detection predicts early metastatic relapse after neoadjuvant chemotherapy in large operable and locally advanced breast cancer in a phase II randomized trial." Clin Cancer Res. Nov. 1, 2008; 14 (21):7004-10.
Rastelli et al., "Factors predictive of response to hormone therapy in breast cancer." May 1, 2008, 94(3): 370-383.
Ross & Slodkowska, "Circulating and disseminated tumor cells in the management of breast cancer." Am J Clin Pathol. Aug. 2009; 132(2):237-45.
Tewes et al., "Molecular profiling and predictive value of circulating tumor cells in patients with metastatic breast cancer: an option for monitorying response to breast cancer related therapies." Breast Cancer Research and Treatment, Aug. 5, 2008, 115(3): 581-590.
Wulfing et al., "HER2-positive circulating tumor cells indicate poor clinical outcome in stage I to III breast cancer patients." Clin Cancer Res. Mar. 15, 2006; 12(6):1715-20.

* cited by examiner

Fig. 1
% of cells positive for ER
| | No POS = 0 | Cytopl POS = 0 | Slight POS, but nuclear POS = +1 | Strong nuclear POS = +2 |
|---|---|---|---|---|
| MCF-7* + Anti-ER Ab | 5% | 9% | 11% | 75% |
Heterogeneous ER in MCF-7*
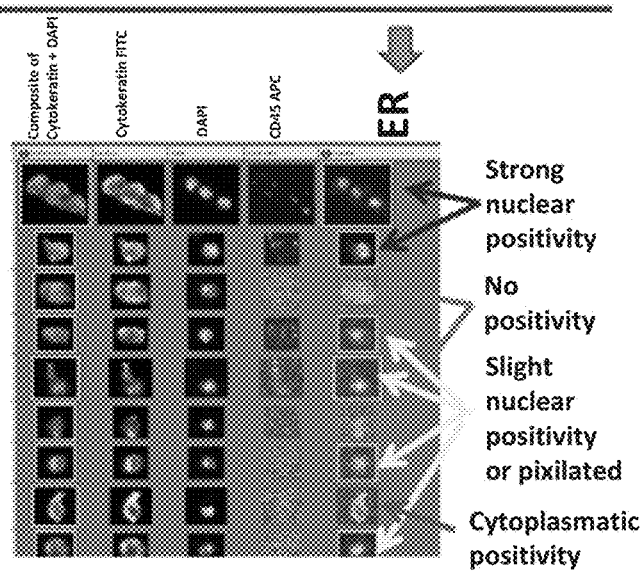
Strong nuclear positivity
No positivity
Slight nuclear positivity or pixilated
Cytoplasmatic positivity
ER for MCF-7* and SK-Br-3
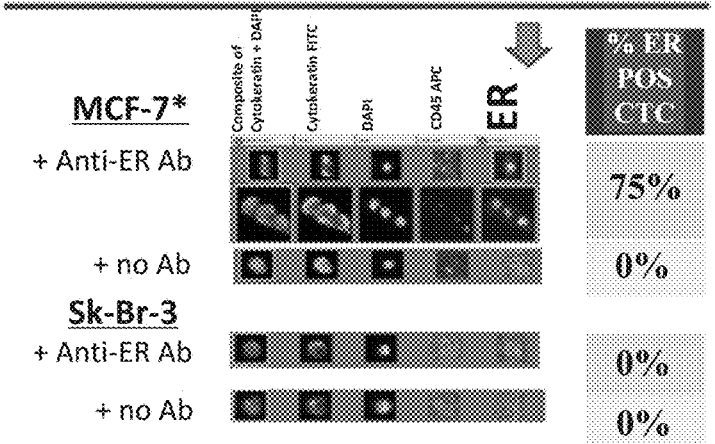
CTC-Assigned Biologic Points

A

Fig. 2 (Cont.)
B
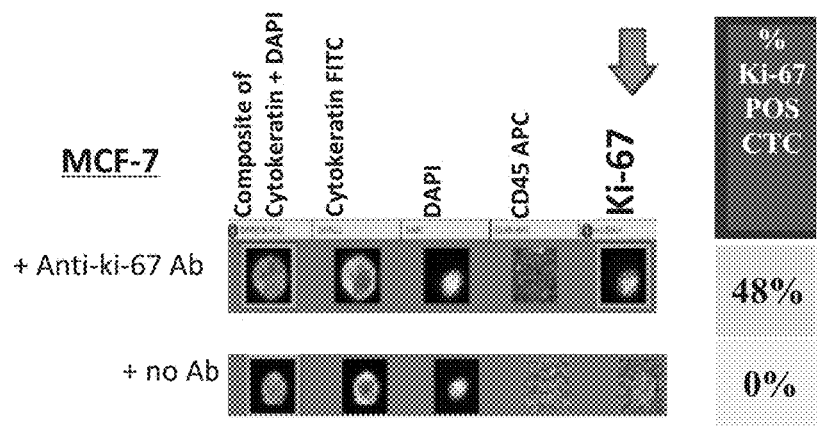
C
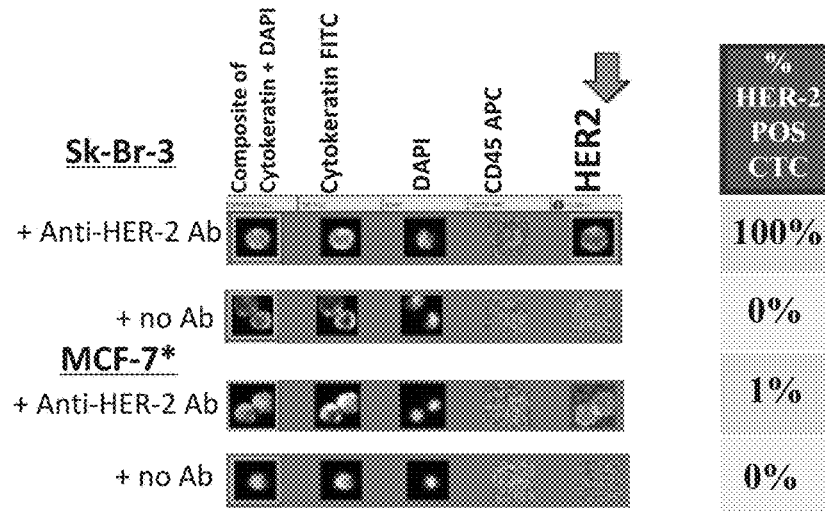

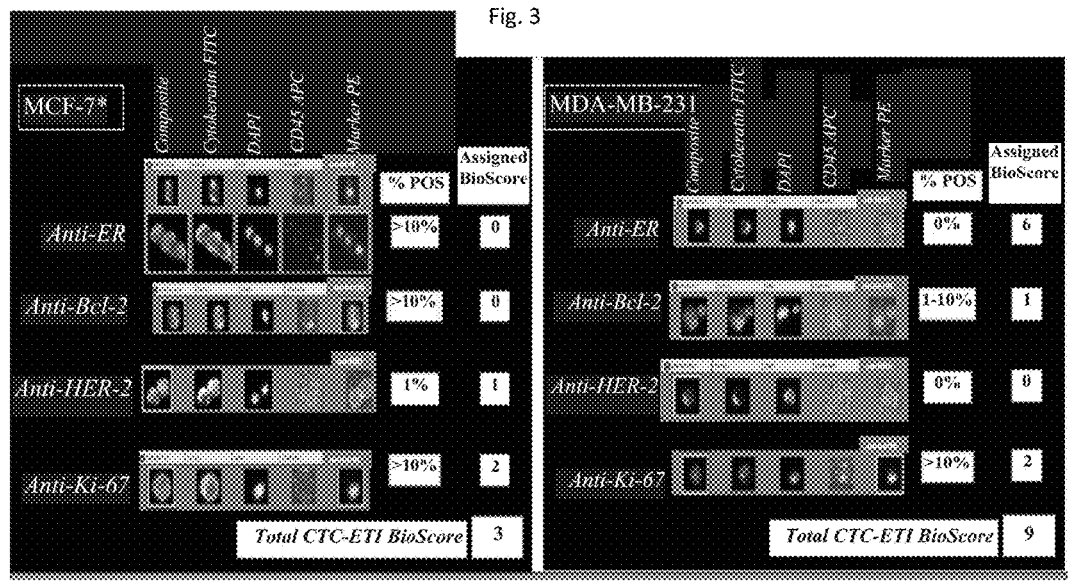

Fig. 4

Patient #1 (Tissue: ER POS, HER-2 NEG)

| Tube | # Cells/7.5 ml/Tube | | Total CTC Points |
|---|---|---|---|
| | # of CTC/Tube | Mean of CTC/7.5 ml | |
| ER | 811 | | |
| Bcl-2 | 934 | 3362/4 = 840 | 2 |
| HER-2 | 841 | | |
| Ki-67 | 776 | | |

| Marker | Composite | Marker PE | % CTC positive | Assigned Bio-Points | Total bio-points |
|---|---|---|---|---|---|
| ER | | | 61 | 0 | |
| Bcl-2 | | | 38 | 0 | 2 |
| HER-2 | | | 0 | 0 | |
| Ki-67 | | | 50 | 2 | |

CTC-ETI = 4
*Int*

Patient #2 (Tissue: ER POS, HER-2 NEG)

| Tube | # Cells/7.5 ml/Tube | | Total CTC points |
|---|---|---|---|
| | # of CTC/Tube | Mean of CTC/Tube | |
| ER | 6 | | |
| Bcl-2 | 5 | 25/4 ~ 6 | 1 |
| HER-2 | 6 | | |
| Ki-67 | 8 | | |

| Marker | Composite | Marker PE | % CTC positive | Assigned Bio-Points | Total bio-points |
|---|---|---|---|---|---|
| ER | | | 33 | 0 | |
| Bcl-2 | | | 60 | 0 | 2 |
| HER-2 | | | 0 | 0 | |
| Ki-67 | | | 12 | 2 | |

CTC-ETI = 3
*Low*

Patient #3 (Tissue: ER POS, HER-2 NEG)

| Tube | # of Cells/7.5 ml/Tube | | Total CTC Points |
|---|---|---|---|
| | # of CTC/Tube | Mean of CTC/7.5 ml | |
| ER | 8 | | |
| Bcl-2 | 16 | 14 | 2 |
| HER-2 | 17 | | |
| Ki-67 | 15 | | |

CTC-ETI = 10
*High*

| Markers | Composite | Marker PE | % CTC positive | Assigned Bio-Points | Total bio points |
|---|---|---|---|---|---|
| ER | | | 0% | 6 | |
| Bcl-2 | | | 62% | 0 | 8 |
| HER-2 | | | 0% | 0 | |
| Ki-67 | | | 20% | 2 | |

Fig. 7

| | Stage 1 | Stage 2 | | |
|---|---|---|---|---|
| | | Group 1 | Group 2 | Group 3 |
| Date of start | 01/19/2011 | 03/15/2011 | 03/29/2011 | |
| N= | 8 | 7 | 6 | |
| Entered | 8 | 7 | 6 | |
| Eligible | 8 | 6 (1 screen failure ER-: pt 11) | 5 | |
| Mean + CTC≥5 | 5 | 5 | 4 | |
| Success of CTC-ETI | 5 | 3 (pts: #12, #13, #14) | 1 (pt #16) | |
| Machine/technical failure) | X | 1 (pt# 15) | 1 (pt# 20) | |
| Without Success | N/A | 2   ER  BCL-2  Ki-67  HER-2<br>Pt 10  ✓  ✓      ✓  Low count<br>Pt 15  ✓  X (tech failure)  ✓  ✓<br>3/5 successs | 3   ER  HER-2  Ki-67  BCL-2<br>Pt 17  ✓  ✓     ✓  Low count<br>Pt 19  ✓  ✓     ✓  Low count<br>Pt 20  X  X     ✓  X<br>1/4 success (group2) + 3/5 success (group 1) = 4/9 success (group1 + group 2) | |

DIAGNOSIS AND TREATMENT OF BREAST CANCER

This application is a continuation of U.S. patent application Ser. No. 13/178,128, filed Jul. 7, 2011, which claims priority to provisional applications 61/362,021, filed Jul. 7, 2010 and 61/469,890, filed Mar. 31, 2011, each of which are herein incorporated by reference in its entirety.

FIELD OF THE INVENTION

The present invention relates to compositions and methods for cancer diagnosis, research and therapy, including but not limited to, cancer markers. In particular, the present invention relates to compositions and methods for the prediction of a subject's response to cancer therapies.

BACKGROUND OF THE INVENTION

Breast cancer is the second most common form of cancer among women in the U.S., and the second leading cause of cancer deaths among women. While the 1980s saw a sharp rise in the number of new cases of breast cancer, that number now appears to have stabilized. The drop in the death rate from breast cancer is probably due to the fact that more women are having mammograms. When detected early, the chances for successful treatment of breast cancer are much improved.

Breast cancer, which is highly treatable by surgery, radiation therapy, chemotherapy, and hormonal therapy, is most often curable when detected in early stages. Mammography is the most important screening modality for the early detection of breast cancer. Breast cancer is classified into a variety of sub-types, but only a few of these affect prognosis or selection of therapy. Patient management following initial suspicion of breast cancer generally includes confirmation of the diagnosis, evaluation of stage of disease, and selection of therapy. Diagnosis may be confirmed by aspiration cytology, core needle biopsy with a stereotactic or ultrasound technique for nonpalpable lesions, or incisional or excisional biopsy. At the time the tumor tissue is surgically removed, part of it is processed for determination of ER and PR levels.

Prognosis and selection of therapy are influenced by the age of the patient, stage of the disease, pathologic characteristics of the primary tumor including the presence of tumor necrosis, estrogen-receptor (ER) and progesterone-receptor (PR) levels in the tumor tissue, HER2 over expression status and measures of proliferative capacity, as well as by menopausal status and general health. Overweight patients may have a poorer prognosis (Bastarrachea et al., Annals of Internal Medicine, 120: 18 [1994]). Prognosis may also vary by race, with blacks, and to a lesser extent Hispanics, having a poorer prognosis than whites (Elledge et al., Journal of the National Cancer Institute 86: 705 [1994]; Edwards et al., Journal of Clinical Oncology 16: 2693 [1998]).

The three major treatments for breast cancer are surgery, radiation, and drug therapy. No treatment fits every patient, and often two or more are required. The choice is determined by many factors, including the age of the patient and her menopausal status, the type of cancer (e.g., ductal vs. lobular), its stage, whether the tumor is hormone-receptive or not, and its level of invasiveness.

Breast cancer treatments are defined as local or systemic. Surgery and radiation are considered local therapies because they directly treat the tumor, breast, lymph nodes, or other specific regions. Drug treatment is called systemic therapy, because its effects are wide spread. Drug therapies include classic chemotherapy drugs, hormone blocking treatment (e.g., aromatase inhibitors, selective estrogen receptor modulators, and estrogen receptor down regulators), and monoclonal antibody treatment (e.g., against HER2). They may be used separately or, most often, in different combinations.

There is a need for additional treatments, particularly treatments customized to a patient's tumor.

SUMMARY OF THE INVENTION

The present invention relates to compositions and methods for cancer diagnosis, research and therapy, including but not limited to, cancer markers. In particular, the present invention relates to compositions and methods for the prediction of a subject's response to cancer therapies.

In some embodiments, the compositions and methods of the present invention find use in determining a subject's (e.g., a subject diagnosed with metastatic breast cancer) prognosis of survival or response to treatment (e.g., anti-estrogen treatment). Such methods find use in both research and clinical applications.

For example, in some embodiments, the present invention provides a method for determining a treatment course of action, comprising detecting the level of circulating tumor cells (CTC) in a sample from a subject diagnosed with metastatic breast cancer; and determining a treatment course of action based on the level of CTC in the sample. In some embodiments, the treatment course of action comprises anti-estrogen therapy (e.g., tamoxifen or an aromatase inhibitor such as letrozole, anastrozole, or exemestane). In other embodiments, the treatment course of action comprises chemotherapy. In some embodiments, the method further comprises the step of characterizing one or more tumor markers associated with CTC (e.g., estrogen receptor, HER-2, bcl-2, apoptosis markers, IGFR1, vimentim, or ki67). In some embodiments, the apoptosis marker is detected using monoclonal antibody M30. In some embodiments, the metastatic breast cancer is estrogen receptor positive. In some embodiments, one or more of the tumor markers are detecting using a multiplex technology (e.g., multiplex PCR) or immunomagnetic assay. In some embodiments, assays are automated. In some embodiments, the method further comprises the step of determining a CTC-Endocrine Therapy Index (CTC-ETI) is determined. In some embodiments, the CTC-ETI is calculated by assigning points to levels of CTC and tumor markers. In some embodiments, a low CTC-ETI is indicative of a subject that is likely to respond to endocrine (e.g., anti-estrogen) therapy. In some embodiments, a high CTC-ETI score is indicative of a subject that is not likely to respond to endocrine therapy and is better treated with chemotherapy.

BRIEF DESCRIPTION OF THE DRAWINGS

FIG. 1 shows expression of estrogen receptor in cancer cell lines.

FIG. 3 shows calculation of CTC-ETI scores for cancer cell lines.

FIG. 4 shows calculation of CTC-ETI scores for three patients.

FIG. 7 shows a schematic for an exemplary clinical study of CTC-ETI scores and clinical outcome in breast cancer.

FIG. 8 shows the results of a clinical study of 8 patients that monitored CTC-ETI scores.

DEFINITIONS

Figure 2:
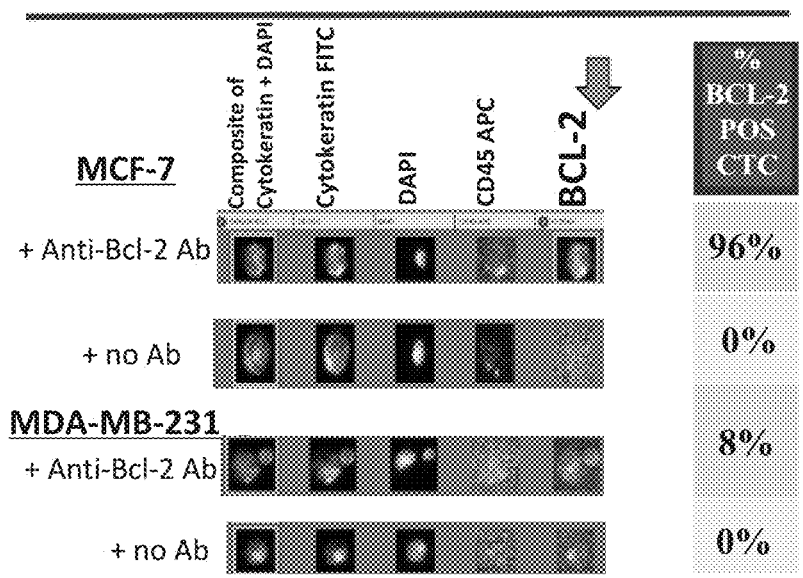
FIG. 2 shows expression of a) Bcl-2, b) Ki-67 and c) HER-2 in cancer cell lines.
Figure 5:
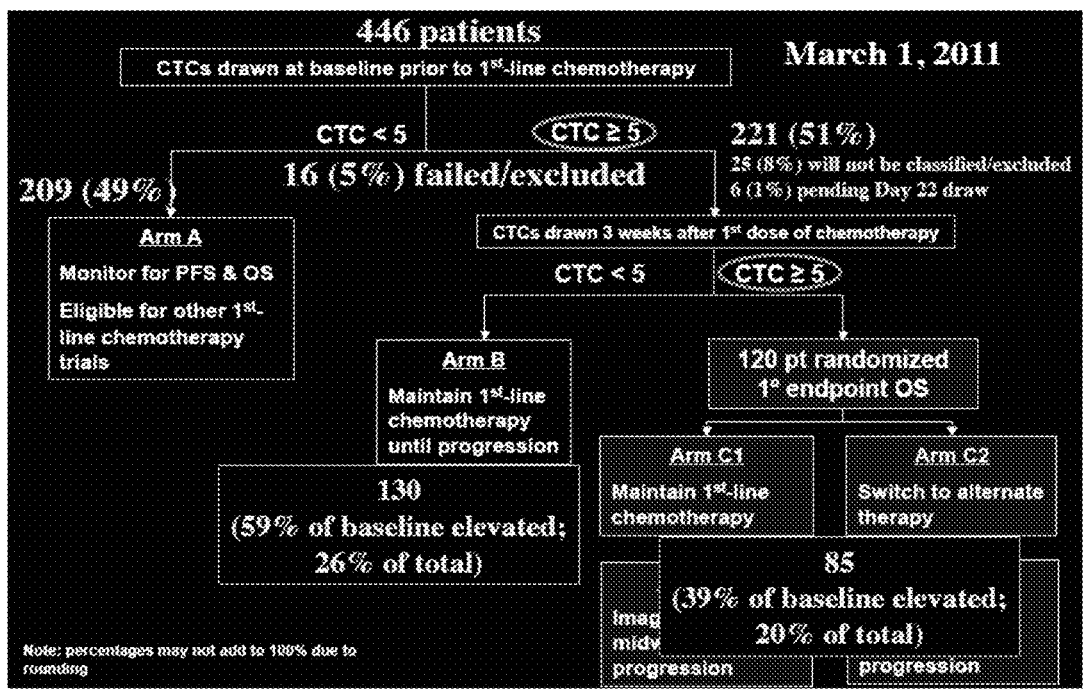
FIG. 5 shows a schematic for an exemplary clinical study of CTC-ETI scores and clinical outcome in breast cancer.
Figure 6:
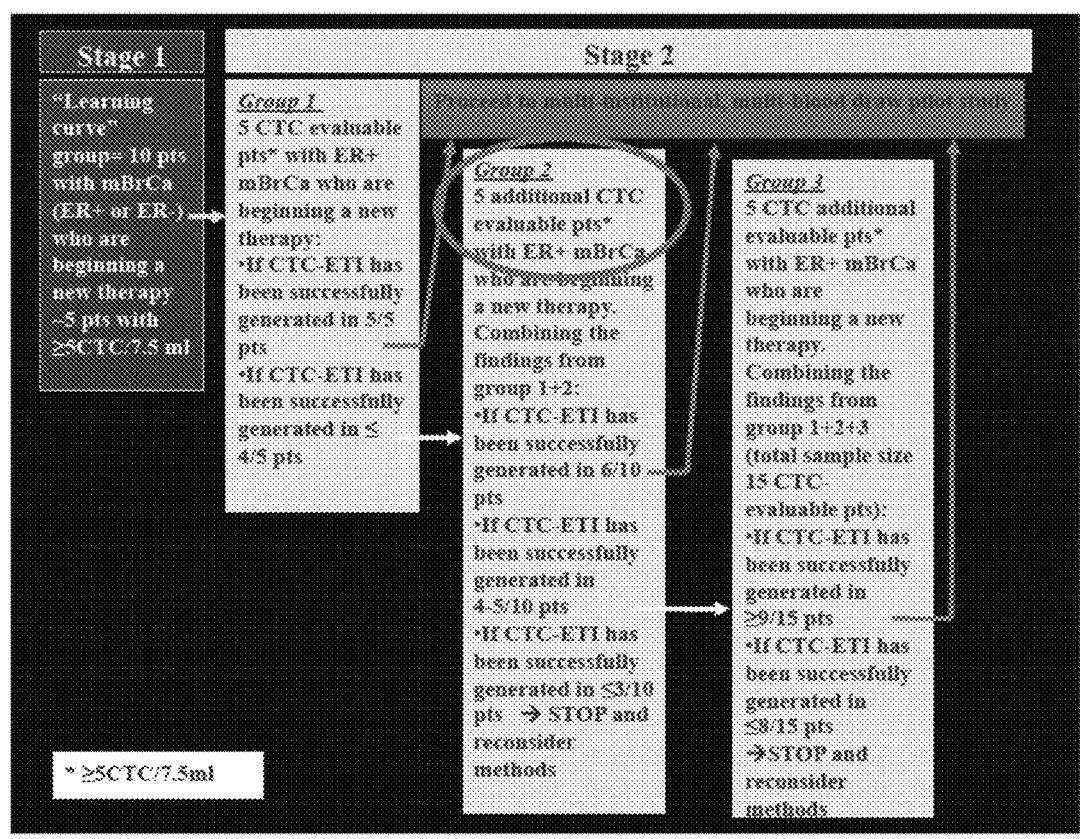
FIG. 6 shows a schematic for an exemplary clinical study of CTC-ETI scores and clinical outcome in breast cancer.

To facilitate an understanding of the present invention, a number of terms and phrases are defined below:

As used herein, the terms "detect", "detecting", or "detection" may describe either the general act of discovering or discerning or the specific observation of a composition.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the Tm of the formed hybrid, and the G:C ratio within the nucleic acids. A single molecule that contains pairing of complementary nucleic acids within its structure is said to be "self-hybridized."

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under "medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l NaH2PO4 H2O and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1× SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l NaH2PO4 H2O and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l NaH2PO4 H2O and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

As used herein, the term "amplification oligonucleotide" refers to an oligonucleotide that hybridizes to a target nucleic acid, or its complement, and participates in a nucleic acid amplification reaction. An example of an amplification oligonucleotide is a "primer" that hybridizes to a template nucleic acid and contains a 3' OH end that is extended by a polymerase in an amplification process. Another example of an amplification oligonucleotide is an oligonucleotide that is not extended by a polymerase (e.g., because it has a 3' blocked end) but participates in or facilitates amplification. Amplification oligonucleotides may optionally include modified nucleotides or analogs, or additional nucleotides that participate in an amplification reaction but are not complementary to or contained in the target nucleic acid. Amplification oligonucleotides may contain a sequence that is not complementary to the target or template sequence. For example, the 5' region of a primer may include a promoter sequence that is non-complementary to the target nucleic acid (referred to as a "promoter-primer"). Those skilled in the art will understand that an amplification oligonucleotide that functions as a primer may be modified to include a 5' promoter sequence, and thus function as a promoter-primer. Similarly, a promoter-primer may be modified by removal of, or synthesis without, a promoter sequence and still function as a primer. A 3' blocked amplification oligonucleotide may provide a promoter sequence and serve as a template for polymerization (referred to as a "promoter-provider").

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (e.g., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products.

Preferably, the primer is an oligodeoxyribonucleotide. The primer should be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to at least a portion of another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

DETAILED DESCRIPTION OF THE INVENTION

The present invention relates to compositions and methods for cancer diagnosis, research and therapy, including but not limited to, cancer markers. In particular, the present invention relates to compositions and methods for the prediction of a subject's response to cancer therapies.

Mortality from breast cancer has declined in the Western world over the last 30 years, due in part to widespread application of adjuvant systemic therapy. However, more than 40,000 women will die of metastatic breast cancer in the United States in 2008. While an occasional patient with metastatic breast cancer appears to be cured, most are destined to ultimately die of their disease. Nonetheless, a number of new therapies have been introduced for patients in this setting, resulting in modest prolongation of survival and substantial improvements in palliation.

Thus, the goal of therapy for most patients with metastatic breast cancer is choosing the therapy with the highest likelihood of response and the lowest possibility of toxicity, thus balancing symptoms of the cancer with side effects of treatment. Indeed, a wide array of strategies and agents are now available to treat these patients. These include chemotherapy (there are now more than 10 different agents approved for treatment of metastatic breast cancer), as well as anti-HER2 therapy (trastuzumab, lapatinib), and although not approved by the FDA, anti-angiogenic therapies also appear quite promising. However, one of the mainstays of treatment of patients with metastatic breast cancer is anti-estrogen therapy.

Breast cancer can be treated with a variety of anti-estrogen approaches, which can basically be divided into additive and ablative. The most commonly used additive therapy is the selective estrogen receptor modulator (SERM), tamoxifen, although androgenic therapies such as fluoxymesterone and progestational agents, such as megestrol acetate, are also effective. Ablative therapies were, in the past, principally surgical, but more recently have been accomplished in premenopausal women with luteinizing hormone releasing hormone agonists and antagonists, such as goserlin or leuprolide, and in post-menopausal women with agents that inhibit the aromatase-induced conversion of the precursors dihydroepiandrostenidione (DHEA) and testosterone to estradiol and estrone. There are three available aromatase inhibitors (AIs) in the US: letrozole, anastrozole, and exemestane.

Selection of appropriate treatment for patients with metastatic breast cancer is based on two factors: prognosis and prediction. In this regard, anti-estrogen therapy can be considered the earliest of the "targeted" therapies. Subsequent studies have demonstrated that tamoxifen is inactive in patients with ER negative breast cancers. However, anti-estrogen treatments are effective in only 30-50% of women with ER positive (or "rich") tumors in either the metastatic or early settings. It is contemplated that those patients with ER positive, yet endocrine refractory, metastatic breast cancer would be better served with immediate chemotherapy, in spite of its increased toxicity profile, rather than delaying chemotherapy during a several month trial of ineffective, albeit less toxic, endocrine treatment.

Once a palliative treatment regimen is selected for a patient with metastatic breast cancer, it is discontinued and the patient started on a new therapy for one of two reasons: 1) the chosen therapy is so toxic that even if it works it is unlikely to induce palliation; or 2) it does not work and the tumor progresses. Current methods of determining these phenomena, especially the latter, include history, physical examination, serologic testing, and radiographic evaluation. History and physical examination are notoriously unreliable, due to subjectivity issues and the fact that more than 50% of patients have only metastatic lesions in internal organs, such as bone, liver, and lung. Non-specific serologic examinations, such as enzymes derived from bone (alkaline phosphatase) and liver (alkaline phosphatase, Serum glutamate oxalate transferase, etc) lack both sufficient sensitivity and specificity to be useful in determining progression. At least three categories of tumor-associated tumor markers have been used in monitoring such patients. These include assays for the MUC-1 protein (CA15-3, CA27.29), for carcinoembryonic antigen (CEA), and for the extra-cellular domain of HER2. The American Society of Clinical Oncology Tumor Marker Guideline Panel has recommended that at least CA15-3 and CEA are used in monitoring selected patients with metastatic breast cancer. However, in all three cases, early determination of treatment response or failure is confounded by the phenomenon of a "tumor marker spike", in which the marker actually increases for a few weeks to months before it declines to or below baseline in as many as 25% of patients who are ultimately felt to have responded to therapy. Thus, circulating tumor marker results, to date, are fundamentally without value to determine progression during the first one to two months of a newly started therapy.

Radiographic imaging has been the most highly regarded means of determining clinical course in a patient with metastatic breast cancer. Strict criteria have been developed to define response, stability, and progression for plain radiographs, computerized tomography, and magnetic resonance imaging. However, radiographic imaging has several drawbacks. The sensitivity for progression of all of these modalities is poor for most patients during the first one or two cycles of therapy, and in particular the latter two are inconvenient, expensive, and associated with discomfort for the patient. Therefore, these tests are usually not performed until several months into a patient's course after starting a new therapy. Perhaps more importantly, only approximately 50% of patients with metastatic breast cancer will have "measurable" disease-rather, they will have "non-measurable" lesions in bone and/or pleura or "military" lesions in skin and lung that are too small to accurately quantify. Efforts to monitor patients with "bone-only" disease have been particularly frustrating. Bone scintigraphy with technicium pyrophosphate is the most widely used imaging modality to monitor these patients, but it is limited by relatively poor sensitivity for detection of progression and by the so-called "scintigraphic flare," in which patients who are responding to therapy, in particular endocrine therapy, are found to have increased radio-tracer uptake in known lesions and even the appearance of new areas of uptake as a function of increased osteoblastic healing activity.

There are selected patients in whom rapid progression is easily determined by clinical, serologic, and/or radiologic means. However, many patients with metastatic breast cancer present a clinical challenge in determination of whether a newly initiated therapy is likely to be successful over the succeeding several months or it is a futile regimen. If so, such patients would be better treated with a potentially more effective, even if more toxic, treatment, such as chemotherapy.

Accordingly, in some embodiments, the present invention provides methods of identifying patients with ER positive metastatic breast cancer that are not likely to respond to anti estrogen therapies. In such patients, traditional chemotherapy can be started immediately or after a brief trial of anti-estrogen therapy. In some embodiments, the methods of the present invention allow for earlier monitoring of effectiveness of current treatment. In such, situations, alternative treatments can be chosen for subjects that are not responding to their current treatment.

In some embodiments, the present invention provides methods utilizing the analysis of circulating tumor cells (CTC). For example, in some embodiments, the present invention provides methods of determining the effectiveness of anti-estrogen therapy by quantitating levels of CTC. In some embodiments, the level of CTC is used to determine prognosis and guide treatment course of action.

In some embodiments, CTC levels are compared to the levels of a subject who does not have cancer or a population average of subjects not diagnosed with cancer. In some embodiments, CTC are compared to population averages of subjects diagnosed with metastatic breast cancer, including subjects that have responded to anti-estrogen therapies and those that have not. In other embodiments, the levels of CTC in a subject diagnosed with metastatic or non-metastatic breast cancer are monitored over time.

In other embodiments, one or more tumor markers associated with CTC are characterized in order to distinguish women who will do well on anti-estrogen therapy vs those who appear hormone refractory and thus determine a prognosis or treatment course of action. In some embodiments, the tumor markers include, but are not limited to, ER, HER2, bcl-2, apoptosis (staining with monoclonal M30), IGRFR1, vimentin and Ki67. Additional tumor markers may be utilized and are known to those of skill in the art. The present invention contemplates both known and unknown (e.g., yet to be discovered) tumor markers. Preferred tumor markers are those that are present on CTC and are indicative (alone or in combination) of response to anti-estrogen therapy.

In some embodiments, the status of tumor markers on CTC is correlated with the status of these same markers in primary and/or metastatic tissue collected from the same patients.

I. Circulating Tumor Cells

Tumor cells were first recognized in human circulation, albeit postmortem, more than 150 years ago. Recent advances in technology have permitted the development of a highly automated and standardized system to separate circulating tumor cells (CTC) from whole blood with the use of an immunomagnetic approach. In some embodiments, methods of the present invention utilize the CellSearch™ system, (Immunicon Corporation, Huntingdon Valley, Pa.) to quantitate CTC (Allard et al., Clin Cancer Res 2004; 10 (20):6897-904; Cristofanilli et al., N Engl J Med 2004; 351 (8):781-91; each of which is herein incorporated by reference in its entirety). The CELL SEARCH system identifies "events" that are then characterized as epithelial in origin by immunofluorescent staining with anti-cytokeratin antibodies and determined to be cellular by virtue of staining with DAPI. Contaminating leucocytes are identified with immunofluorescent staining with a monoclonal antibody against CD45, and the results are displayed pictorially in a digital format.

The present invention is not limited to the use of the CELL SEARCH system. Any method of isolating and/or quantitating CTC may be utilized.

II. Tumor Markers

In some embodiments, the present invention provides methods of identifying tumor markers associated with CTC. Exemplary tumor markers are described in more detail below.

Estrogen receptor (ER). Among others, selected markers that indicate independence from estrogen therapy include relative levels of ER, HER2, bcl-2, and measures of apoptosis. Several studies have suggested that the association between ER expression and benefit from endocrine therapy is not dichotomous, but rather is related to the quantitative level of the ER protein. Accordingly, different cutoffs have been used to dichotomize "positive" from "negative" for different assays of ER. In some embodiments, relative levels of ER, which can be measured in CTCs, are used to aid in determining the likelihood of response to endocrine therapy.

HER2. A variety of pre-clinical and clinical investigations have indicated that HER2 over-expression and/or amplification decreases sensitivity to estrogen treatment sensitivity in ER positive breast cancer. The present invention is not limited to a particular mechanism. Indeed, an understanding of the mechanism is not necessary to practice the present invention. Nonetheless, it is contemplated that patients who have ER positive, but also HER2 positive, breast cancer are less likely to benefit from anti-estrogen treatments.

BCL-2. BCL-2 is an anti-apoptotic protein that protects a cell from entering the programmed cell-death pathway. BCL-2 is commonly expressed in breast cancer, and is associated with worse prognosis. BCL-2 expression is more commonly expressed in ER positive than ER negative breast cancers. Pre-clinical and some clinical studies indicate that BCL-2 expression appears to be associated with relative resistance to anti-estrogen therapy. The present invention is not limited to a particular mechanism. Indeed, an understanding of the mechanism is not necessary to practice the present invention. Nonetheless, it is contemplated that ER positive, BCL-2 positive breast cancers are more likely to be refractory to endocrine treatments.

Apoptosis. One mechanism of action of anti-estrogen therapy is mediated via programmed cell death with apoptosis. Therefore, serial monitoring of apoptosis provides evidence of breast cancer cell death. Pre-operative studies of both chemotherapy and hormone therapy have documented that early induction of apoptosis is associated with subsequent clinical response. The present invention is not limited to a particular mechanism. Indeed, an understanding of the mechanism is not necessary to practice the present invention. Nonetheless, it is contemplated that serial evaluation of apoptosis provides an indication of the effectiveness of anti-estrogen therapy.

KI-67. Ki67 is a proliferation antigen that reflects cellular turnover. Ki67 immunohistochemistry staining in primary tissues is associated with prognosis in early stage breast cancer. In neoadjuvant studies, reduction in Ki67 levels has been related to apparent benefit from anti-estrogen therapies, including both tamoxifen and the aromatase inhibitors. The present invention is not limited to a particular mechanism. Indeed, an understanding of the mechanism is not necessary to practice the present invention. Nonetheless, it is contemplated that serial evaluation of Ki67 associated with CTC before and during endocrine treatment provides an indication of the likelihood of benefit.

In some embodiments, one or more of the above named markers is detected in a multiplex or panel format. For example, in some embodiments, a multi-parameter rt-PCR-based assay such as OncotypeDX™ (Genomic Health Inc, CA) is utilized. Relative values of ER, BCL-2, HER2, and Ki67 expression drive the algorithm used to derive the OncotypeDx "Recurrence Score (RS)." Highly validated correlative studies have demonstrated that both node negative and node positive patients with low RS, reflecting high ER, low HER2, low BCL-2, and low Ki67 have a prognosis when treated with tamoxifen alone, while those with high recurrence score, reflecting low ER, high HER2, high BCL-2, and high Ki67 have a much worse prognosis when treated with tamoxifen alone but are much more likely to benefit from chemotherapy (Paik et al., N Engl J Med 2004; 351:2817-26; Paik et al., J Clin Oncol 2006; 24:3726-34).

III. Detection Methods

Exemplary methods of detecting markers associated with CTCs are provided below. However, any suitable method of detecting tumor marker nucleic acids or proteins may be utilized.

A. DNA and RNA Detection

In some embodiments, tumor markers are detected as mRNA using a variety of nucleic acid techniques known to those of ordinary skill in the art, including but not limited to: nucleic acid sequencing; nucleic acid hybridization; and, nucleic acid amplification.

1. Sequencing

Illustrative non-limiting examples of nucleic acid sequencing techniques include, but are not limited to, chain terminator (Sanger) sequencing and dye terminator sequencing. Those of ordinary skill in the art will recognize that because RNA is less stable in the cell and more prone to nuclease attack experimentally RNA is usually reverse transcribed to DNA before sequencing.

Chain terminator sequencing uses sequence-specific termination of a DNA synthesis reaction using modified nucleotide substrates. Extension is initiated at a specific site on the template DNA by using a short radioactive, or other labeled, oligonucleotide primer complementary to the template at that region. The oligonucleotide primer is extended using a DNA polymerase, standard four deoxynucleotide bases, and a low concentration of one chain terminating nucleotide, most commonly a di-deoxynucleotide. This reaction is repeated in four separate tubes with each of the bases taking turns as the di-deoxynucleotide. Limited incorporation of the chain terminating nucleotide by the DNA polymerase results in a series of related DNA fragments that are terminated only at positions where that particular di-deoxynucleotide is used. For each reaction tube, the fragments are size-separated by electrophoresis in a slab polyacrylamide gel or a capillary tube filled with a viscous polymer. The sequence is determined by reading which lane produces a visualized mark from the labeled primer as you scan from the top of the gel to the bottom.

Dye terminator sequencing alternatively labels the terminators. Complete sequencing can be performed in a single reaction by labeling each of the di-deoxynucleotide chain-terminators with a separate fluorescent dye, which fluoresces at a different wavelength.

2. Hybridization

Illustrative non-limiting examples of nucleic acid hybridization techniques include, but are not limited to, in situ hybridization (ISH), microarray, and Southern or Northern blot.

In situ hybridization (ISH) is a type of hybridization that uses a labeled complementary DNA or RNA strand as a probe to localize a specific DNA or RNA sequence in a portion or section of tissue (in situ), or, if the tissue is small enough, the entire tissue (whole mount ISH). DNA ISH can be used to determine the structure of chromosomes. RNA ISH is used to measure and localize mRNAs and other transcripts within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with either radio-, fluorescent- or antigen-labeled bases is localized and quantitated in the tissue using either autoradiography, fluorescence microscopy or immunohistochemistry, respectively. ISH can also use two or more probes, labeled with radioactivity or the other non-radioactive labels, to simultaneously detect two or more transcripts.

2.1 FISH

In some embodiments, tumor marker sequences are detected using fluorescence in situ hybridization (FISH). The preferred FISH assays for the present invention utilize bacterial artificial chromosomes (BACs). These have been used extensively in the human genome sequencing project (see Nature 409: 953-958 (2001)) and clones containing specific BACs are available through distributors that can be located through many sources, e.g., NCBI. Each BAC clone from the human genome has been given a reference name that unambiguously identifies it. These names can be used to find a corresponding GenBank sequence and to order copies of the clone from a distributor.

Specific protocols for performing FISH are well known in the art and can be readily adapted for the present invention. Guidance regarding methodology may be obtained from many references including: *In situ Hybridization: Medical Applications* (eds. G. R. Coulton and J. de Belleroche), Kluwer Academic Publishers, Boston (1992); *In situ Hybridization: In Neurobiology; Advances in Methodology* (eds. J. H. Eberwine, K. L. Valentino, and J. D. Barchas), Oxford University Press Inc., England (1994); *In situ Hybridization: A Practical Approach* (ed. D. G. Wilkinson), Oxford University Press Inc., England (1992)); Kuo, et al., *Am. J. Hum. Genet.* 49:112-119 (1991); Klinger, et al., *Am. J. Hum. Genet.* 51:55-65 (1992); and Ward, et al., *Am. J. Hum. Genet.* 52:854-865 (1993)). There are also kits that are commercially available and that provide protocols for performing FISH assays (available from e.g., Oncor, Inc., Gaithersburg, Md.). Patents providing guidance on methodology include U.S. Pat. Nos. 5,225,326; 5,545,524; 6,121,489 and 6,573,043. All of these references are hereby incorporated by reference in their entirety and may be used along with similar references in the art and with the information provided in the Examples section herein to establish procedural steps convenient for a particular laboratory.

2.2 Microarrays

Different kinds of biological assays are called microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink-jet printing; or, electrochemistry on microelectrode arrays.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

3. Amplification

Genomic DNA and mRNA may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and 4,800,159; Mullis et al., *Meth. Enzymol.* 155: 335 (1987); and, Murakawa et al., DNA 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399,491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., *Science* 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., *Proc. Natl. Acad. Sci. USA* 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPαS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., *BioTechnol.* 6: 1197 (1988), herein incorporated by reference in its entirety), commonly referred to as Qβ replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990), each of which is herein incorporated by reference in its entirety). For further discussion of known amplification methods see Persing, David H., "In Vitro Nucleic Acid Amplification Techniques" in *Diagnostic Medical Microbiology: Principles and Applications* (Persing et al., Eds.), pp. 51-87 (American Society for Microbiology, Washington, D.C. (1993)).

4. Detection Methods

Non-amplified or amplified tumor marker nucleic acids can be detected by any conventional means. For example, in some embodiments, tumor marker nucleic acids are detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541,205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed in U.S. Pat. No. 6,534,274, herein incorporated by reference in its entirety.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed in U.S. Pat. Nos. 5,925,517 and 6,150,097, herein incorporated by reference in its entirety.

Other self-hybridizing probes are well known to those of ordinary skill in the art. By way of non-limiting example, probe binding pairs having interacting labels, such as those disclosed in U.S. Pat. No. 5,928,862 (herein incorporated by reference in its entirety) might be adapted for use in the present invention. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products in the present invention. See, e.g., U.S. Pat. No. 5,814,447 (herein incorporated by reference in its entirety).

B. Protein Detection

In some embodiments, the present invention provides methods of detecting tumor marker protein and/or levels of tumor marker protein. Proteins are detected using a variety of protein techniques known to those of ordinary skill in the art, including but not limited to: protein sequencing; and, immunoassays.

1. Sequencing

Illustrative non-limiting examples of protein sequencing techniques include, but are not limited to, mass spectrometry and Edman degradation.

Mass spectrometry can, in principle, sequence any size protein but becomes computationally more difficult as size increases. A protein is digested by an endoprotease, and the resulting solution is passed through a high pressure liquid chromatography column. At the end of this column, the solution is sprayed out of a narrow nozzle charged to a high positive potential into the mass spectrometer. The charge on the droplets causes them to fragment until only single ions remain. The peptides are then fragmented and the mass-charge ratios of the fragments measured. The mass spectrum is analyzed by computer and often compared against a database of previously sequenced proteins in order to determine the sequences of the fragments. The process is then repeated with a different digestion enzyme, and the overlaps in sequences are used to construct a sequence for the protein.

In the Edman degradation reaction, the peptide to be sequenced is adsorbed onto a solid surface (e.g., a glass fiber coated with polybrene). The Edman reagent, phenylisothiocyanate (PTC), is added to the adsorbed peptide, together with a mildly basic buffer solution of 12% trimethylamine, and reacts with the amine group of the N-terminal amino acid. The terminal amino acid derivative can then be selectively detached by the addition of anhydrous acid. The derivative isomerizes to give a substituted phenylthiohydantoin, which can be washed off and identified by chromatography, and the cycle can be repeated. The efficiency of each step is about 98%, which allows about 50 amino acids to be reliably determined.

2. Immunoassays

Illustrative non-limiting examples of immunoassays include, but are not limited to immunoprecipitation; Western blot; ELISA; immunohistochemistry; immunocytochemistry; flow cytometry; and, immuno-PCR. Polyclonal or monoclonal antibodies detectably labeled using various techniques known to those of ordinary skill in the art (e.g., colorimetric, fluorescent, chemiluminescent or radioactive) are suitable for use in the immunoassays.

Immunoprecipitation is the technique of precipitating an antigen out of solution using an antibody specific to that antigen. The process can be used to identify protein complexes present in cell extracts by targeting a protein believed to be in the complex. The complexes are brought out of solution by insoluble antibody-binding proteins isolated initially from bacteria, such as Protein A and Protein G. The antibodies can also be coupled to sepharose beads that can easily be isolated out of solution. After washing, the precipitate can be analyzed using mass spectrometry, Western blotting, or any number of other methods for identifying constituents in the complex.

A Western blot, or immunoblot, is a method to detect protein in a given sample of tissue homogenate or extract. It uses gel electrophoresis to separate denatured proteins by mass. The proteins are then transferred out of the gel and onto a membrane, typically polyvinyldifluoride or nitrocellulose, where they are probed using antibodies specific to the protein of interest. As a result, researchers can examine the amount of protein in a given sample and compare levels between several groups.

An ELISA, short for Enzyme-Linked ImmunoSorbent Assay, is a biochemical technique to detect the presence of an antibody or an antigen in a sample. It utilizes a minimum of two antibodies, one of which is specific to the antigen and the other of which is coupled to an enzyme. The second antibody will cause a chromogenic or fluorogenic substrate to produce a signal. Variations of ELISA include sandwich ELISA, competitive ELISA, and ELISPOT. Because the ELISA can be performed to evaluate either the presence of antigen or the presence of antibody in a sample, it is a useful tool both for determining serum antibody concentrations and also for detecting the presence of antigen.

Immunohistochemistry and immunocytochemistry refer to the process of localizing proteins in a tissue section or cell, respectively, via the principle of antigens in tissue or cells binding to their respective antibodies. Visualization is enabled by tagging the antibody with color producing or fluorescent tags. Typical examples of color tags include, but are not limited to, horseradish peroxidase and alkaline phosphatase. Typical examples of fluorophore tags include, but are not limited to, fluorescein isothiocyanate (FITC) or phycoerythrin (PE).

Flow cytometry is a technique for counting, examining and sorting microscopic particles suspended in a stream of fluid. It allows simultaneous multiparametric analysis of the physical and/or chemical characteristics of single cells flowing through an optical/electronic detection apparatus. A beam of light (e.g., a laser) of a single frequency or color is directed onto a hydrodynamically focused stream of fluid. A number of detectors are aimed at the point where the stream passes through the light beam; one in line with the light beam (Forward Scatter or FSC) and several perpendicular to it (Side Scatter (SSC) and one or more fluorescent detectors). Each suspended particle passing through the beam scatters the light in some way, and fluorescent chemicals in the particle may be excited into emitting light at a lower frequency than the light source. The combination of scattered and fluorescent light is picked up by the detectors, and by analyzing fluctuations in brightness at each detector, one for each fluorescent emission peak, it is possible to deduce various facts about the physical and chemical structure of each individual particle. FSC correlates with the cell volume and SSC correlates with the density or inner complexity of the particle (e.g., shape of the nucleus, the amount and type of cytoplasmic granules or the membrane roughness).

Immuno-polymerase chain reaction (IPCR) utilizes nucleic acid amplification techniques to increase signal generation in antibody-based immunoassays. Because no protein equivalence of PCR exists, that is, proteins cannot be replicated in the same manner that nucleic acid is replicated during PCR, the only way to increase detection sensitivity is by signal amplification. The target proteins are bound to antibodies which are directly or indirectly conjugated to oligonucleotides. Unbound antibodies are washed away and the remaining bound antibodies have their oligonucleotides amplified. Protein detection occurs via detection of amplified oligonucleotides using standard nucleic acid detection methods, including real-time methods.

In some embodiments, immunomagnetic detection is utilized. In some embodiments, detection is automated. Exemplary immunomagnetic detection methods include, but are not limited to, those commercially available from Veridex (Raritan, N.J.).

C. Data Analysis

In some embodiments, a computer-based analysis program is used to translate the raw data generated by the detection assay (e.g., the presence, absence, or amount of tumor marker expression and/or level of CTC) into data of predictive value for a clinician (e.g., choice of cancer therapy). The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a blood or serum sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw data, the prepared format may represent a diagnosis or risk assessment (e.g., likelihood of cancer treatment being successful) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system.

The subject may chose further intervention or counseling based on the results. In some embodiments, the data is used for research use. For example, the data may be used to further optimize the inclusion or elimination of markers as useful indicators of a particular condition or stage of disease.

D. Compositions & Kits

Compositions for use in the diagnostic methods of the present invention include, but are not limited to, probes, amplification oligonucleotides, and antibodies. Particularly preferred compositions detect the presence of level of expression of tumor markers in a CTC sample.

Any of these compositions, alone or in combination with other compositions of the present invention, may be provided in the form of a kit. For example, the single labeled probe and pair of amplification oligonucleotides may be provided in a kit for the amplification and detection of tumor markers. Kits may further comprise appropriate controls and/or detection reagents.

The probe and antibody compositions of the present invention may also be provided in the form of an array or panel assay.

IV. Determining a Treatment Course of Action

In some embodiments, the present invention provides systems, kits and methods for determining a treatment course of action.

In some embodiments, a CTC-Endocrine Therapy Index (CTC-ETI) is Determined. In some embodiments, the CTC-ETI is calculated by assigning points to levels of CTC and tumor markers (See e.g., Example 1). In some embodiments, a low CTC-ETI is indicative of a subject that is likely to respond to endocrine (e.g., anti-estrogen) therapy. In some embodiments, a high CTC-ETI score is indicative of a subject that is not likely to respond to endocrine therapy and is better treated with chemotherapy.

EXPERIMENTAL

The following examples are provided to demonstrate and further illustrate certain embodiments of the present invention and are not to be construed as limiting the scope thereof.

Example 1

Development of a CTC-Endocrine Therapy Index (CTC-ETI)

CTC can be reproducibly and reliably enumerated using a commercially-available, automated immunomagnetic system (e.g., CellSearch® system; Veridex LLC). High levels of CTC predict rapid progression in patients with metastatic breast cancer (MBC) (Cristofanilli, et al NEJM 2004). Only ~50% of patients with estrogen receptor (ER) positive MBC benefit from endocrine therapy (ET). Patients with endocrine-refractory MBC are better palliated with chemotherapy. This example describes a multi-parameter assay using CellSearch® that identifies patients with ER positive MBC who are unlikely to benefit from ET and are better served with chemotherapy.

Methods.

The CellSearch® system has four fluorescent channels. Three of these are used to distinguish CTC from WBC (DAPI, anti-cytokeratin, anti-CD45). The $4^{th}$ "empty" channel was used to measure ER, Bcl-2, HER2, and Ki67 expression with antigen-specific fluorescent-labeled antibodies. These four markers were chosen due because of their associations with sensitivity (ER, Bcl-2) or resistance (HER2, Ki-67) to ET. Cultured human breast cancer cells (MCF-7: ER+, BCL-2+, HER2−, Ki67+; MDA-MB-231: ER−, Bcl-2−, HER2−, Ki67+; BT-474: ER+, Bcl-2+, HER2+, Ki67+) were spiked into 7.5 ml human whole blood from normal donors and separated and characterized using the CXC CellSearch® kit.

Table 1 shows association of various markers with response to ET.

TABLE 1

| Phenotype | HIGH Predicts ET: |
|---|---|
| # of CTC | Resistance[1] |
| CTC biology: | |
| ER | Sensitivity[2] |
| Bcl-2 | Sensitivity[3] |
| HER-2 | Resistance[4] |
| Ki-67 | Resistance[5] |

Table 2 shows antibodies and experimental parameters.

TABLE 2

| Marker | Ab (all Mabs) | Source | Control Cell Lines POS | Control Cell Lines NEG | INTEG'N Time |
|---|---|---|---|---|---|
| ER | ER-119.3 | Veridex, LLC | MCF-7* | Sk-Br-3 | 0.222 |
| Bcl-2 | Abel-2/(100) | BD Pharmingen | MCF-7 | MDA-MB-231 | 0.222 |
| HER-2 | Her81 | Veridex, LLC | Sk-Br-3 (3 + IHC) | MCF-7 (1 + IHC) | 0.02 |
| Ki-67 | B56 | BD Pharmingen | MCF-7 | MCF-7* | 0.222 |

Results.

Each cell line stained appropriately for the respective markers, with appropriate negative controls, although staining was heterogeneous, even within a single cell line (FIGS. 1-3).

Using these data, a CTC-ETI, in which scores are assigned to the individual categories consisting of cell counts coupled with the relative percent and degree of cell positivity of each marker, with lower scores (low or no CTC, or CTC with high % and intensity of ER and Bcl-2; low HER2 and Ki-67)=predicted favorable response to ET was developed (Tables 3 and 4).

TABLE 3

| Assume 1-2 CTC point + BioScore point = 3 | | | |
|---|---|---|---|
| CTC-ETI category | CTC-ETI Score | Predicted clinical outcomes for patient on endocrine Rx | Suggested treatment strategy |
| Low | 0-3 | Favorable Respond to ET and/or indolent disease Long TTP | Rx with ET |
| Int | 4-6 | Probably respond or moderately indolent Modest time TTP | Rx with ET |
| High | 7-14 | Poor Resistant to ET Rapid progression | Rx as ER Neg with CTX |

TABLE 4

| CTC Assigned Points Based on CTC Number | | | |
|---|---|---|---|
| | LOW (Good) | INT | HIGH (Bad) |
| # CTC/7.5 ml (mean 4 aliquots) | 0-4 | 5-10 | 10 |
| Assigned Points | 0 | 1 | 2 |

HIGH assigned points = Resistance

| CTC-Assigned Biologic-points: (Assume ≥5 CTC/7.5 mL) | | | | | | |
|---|---|---|---|---|---|---|
| | Good | | Intermediate | | Bad | |
| | % CTC POS | Assign Bio Points | % CTC positive | Assign Bio Points | % CTC positive | Assign Bio Points |
| ER | >10% | 0 | 1-10%[1] | 2 | 0% | 6 |
| Bcl-2 | >10% | 0 | 1-10% | 1 | 0% | 2 |
| HER-2 | 0% | 0 | 1-10% | 1 | >10% | 2 |
| Ki-67 | 0% | 0 | 1-10% | 1 | >10% | 2 |

NOTES:
[1]ER expansion is assigned higher weight than other markers
[2]Total Bio Score range: 0 (ER and Bcl-2 high; HER-2 and Ki-67 neg) to 12 (ER and Bcl-2 neg; HER-2 and Ki-67 High TABLE 4-continued

| | | | CTC-ETI: Final Calculation | | | |
|---|---|---|---|---|---|---|
| | CTC | | BioScore | | | CTC-ETI Score |
| #CTC | Assigned | BioScore | Assigned Points | | | (CTC + BioScore |
| 7.5 lm H/B | Points | Category | Good | Intermed | Bad | Points) |
| 0-4 | 0 | NA | | | | 0 |
| 5-40 | 1 | ER | 0 | 2 | 6 | 1-13 |
| | | Bcl-2 | 0 | 1 | 2 | |
| | | HER-2 | 0 | 1 | 2 | |
| | | Ki-67 | 0 | 1 | 2 | |
| >10 | 2 | ER | 0 | 1 | 6 | 2-14 |
| | | Bcl-2 | 0 | 1 | 2 | |
| | | HER-2 | 0 | 1 | 2 | |
| | | Ki-67 | 0 | 1 | 2 | |

| | | CTC-ETI Categories | |
|---|---|---|---|
| CTC-ETI category | CTC-ETI Score | Predicted clinical outcomes for patient on ET | Suggested Rx strategy |
| Low | 0-3 | Favorable: Response to ET/indolent; Long TTP | ET |
| Int | 4-6 | Probably favorable: Response to ET/indolent: Modest TTP | ET |
| High | 7-14 | Poor; Resistant to ET Rapid progression | ChemoRx (=ER NEG) |

The CTC-ETI was determined for 3 patients with metastatic breast cancer using the methods described above. Results are shown in FIG. 4.

Figure 8:
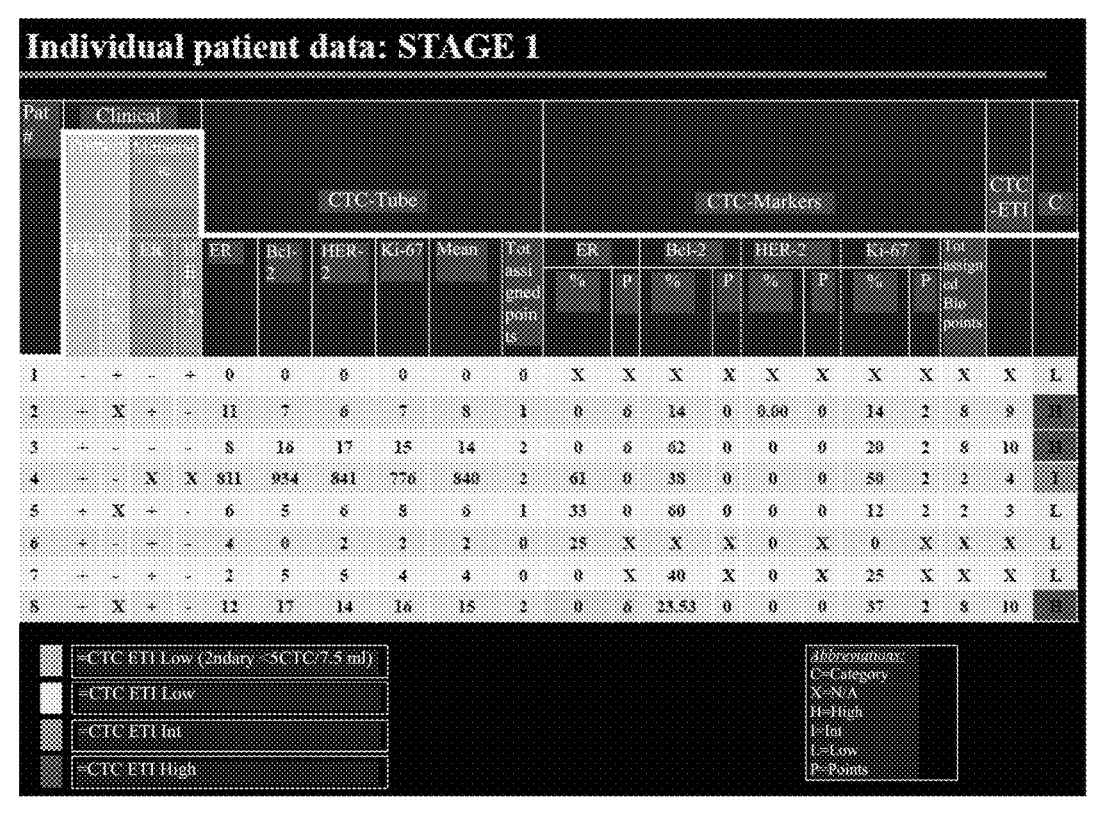
Figure 8:
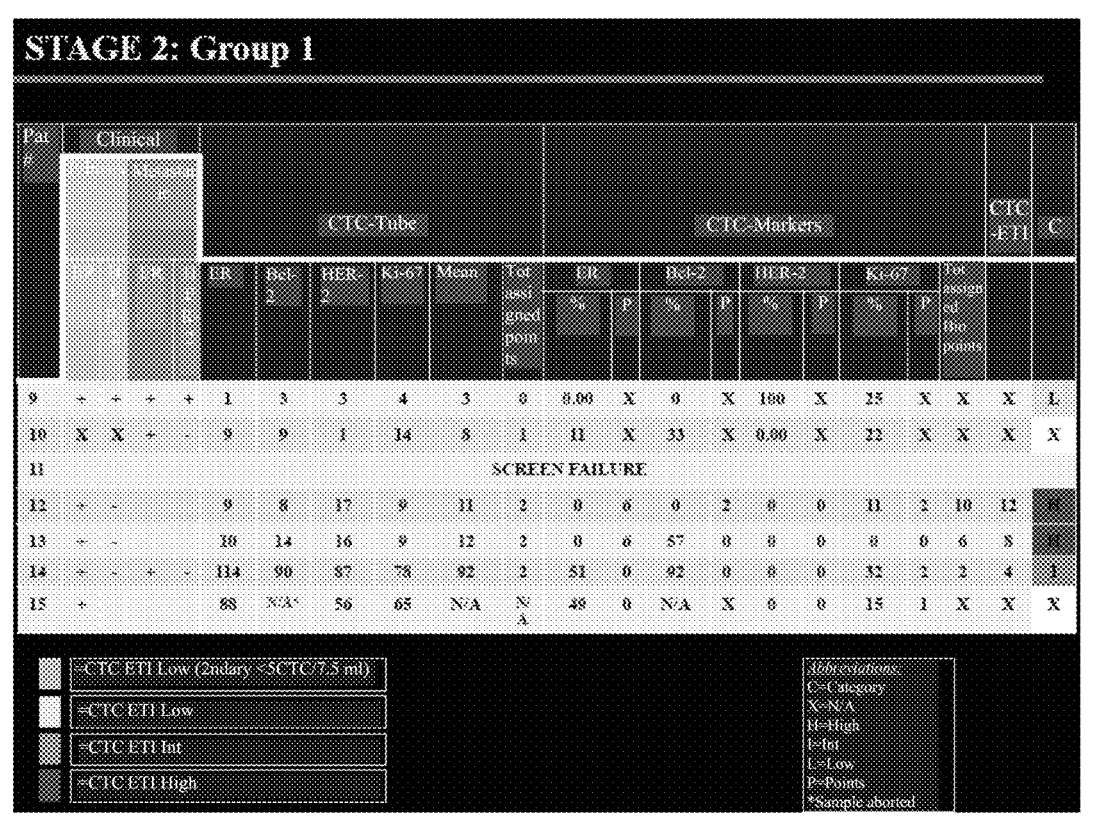
Figure 8:
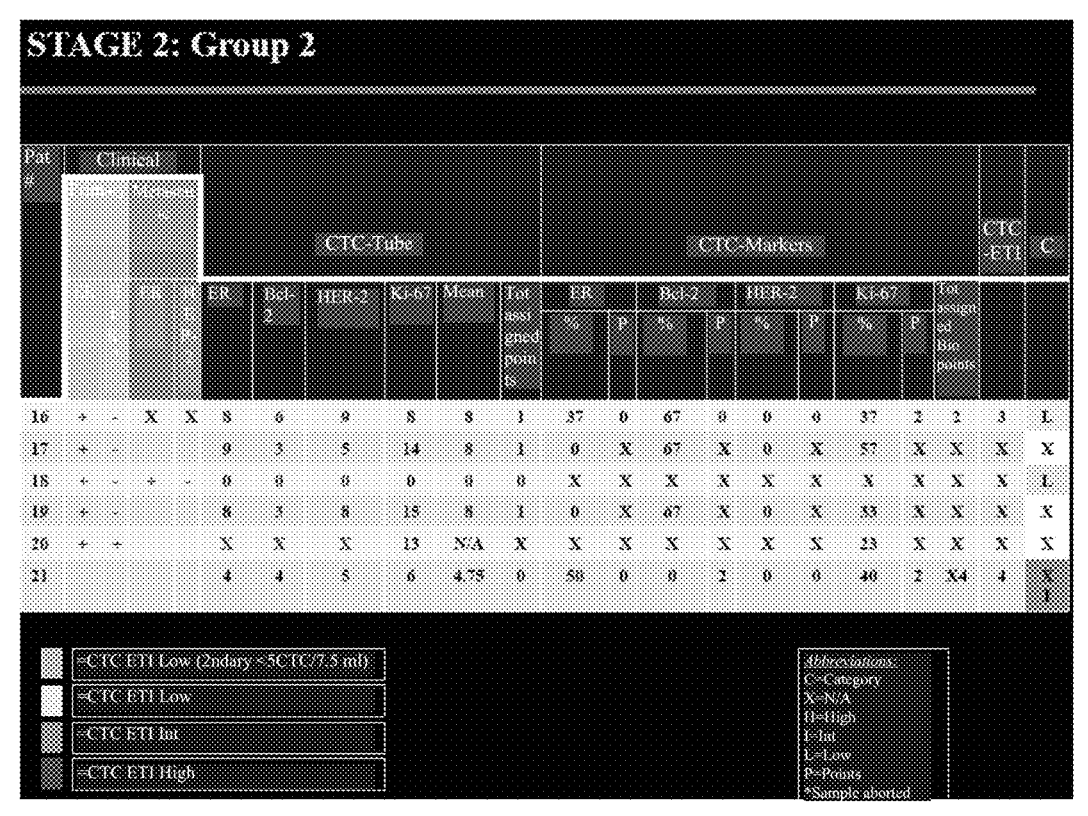

In further studies 21 patients were studied. Study design and results are shown in FIGS. 7-8. One patient was ineligible. Five of 20 pts had low CTC counts (<5 CTC/7.5 ml whole blood), and are expected to have a relatively favorable prognosis. CTC-ETI was determined in 10 pts (50%): 2 pts had low, while 3 had intermediate, and 5 had high CTC-ETI. Technical difficulties precluded accurate CTC-ETI in the remaining 4 patients. Of note, expression of the biomarkers among CTC in single patients was heterogeneous.

Lower CTC-ETI scores (low or no CTC, or CTC with high CTC ER and BCL-2 and low CTC HER2 and Ki-67) are contemplated to be associated with favorable response to ET. CTC-ETI is calculated in patients with MBC to determine if high CTC-ETI predicts resistance and rapid progression on ET.

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

I claim:

1. A method for determining a treatment course of action, comprising
   a) detecting the level of circulating tumor cells (CTC) in a sample from a subject with breast cancer using staining and an immunoassay;
   b) measuring the level of expression of estrogen receptor, HER-2, bcl-2, and ki67 on said CTC using a detection method selected from the group consisting of an immunoassay, nucleic acid amplification, and nucleic acid hybridization;
   c) calculating a numerical CTC-Endocrine Therapy Index (CTC-ETI) based on said number of CTC positive for expression of said estrogen receptor, HER-2, bcl-2, ki67, and total number of CTC, wherein said CTC-ETI is calculated by i) assigning zero points when the number of CTC is 0-4 per 7.5 ml, 1 point when the number of CTC is 5-10 per 7.5 ml, and 2 points when the number of CTC is greater than 10 per 7.5 ml; ii) assigning zero points when the number of CTC positive for estrogen receptor is greater than 10%, assigning 2 point when the number of CTC positive for estrogen receptor is 1-10%, and assigning 6 points when the number of CTC positive for estrogen receptor is zero; iii) assigning zero points when the number of CTC positive for HER-2 is 0%, assigning 1 point when the number of CTC positive for HER-2 is 1-10%, and assigning two points when the number of CTC positive for HER-2 is greater than 10%; iv) assigning zero points when the number of CTC positive for bcl-2 is greater than 10%, assigning 1 point when the number of CTC positive for bcl-2 is 1-10%, and assigning 2 points when the number of bcl-2 is 0%; v) assigning zero points when the number of CTC positive for ki67 is 0%, assigning 1 point when the number of CTC positive for Ki-67 is 1-10%, and assigning 2 points when the number of CTC positive for Ki-67 is greater than 10%; and vi) adding said points to obtain said CTC-ETI; and
   d) administering an anti-estrogen therapy selected from the group consisting of a selective estrogen receptor modulator (SERM) and an aromatase inhibitor when said CTC-ETI is between 0 and 6 and administering chemotherapy when said CTC-ETI is between 7 and 14.

2. The method of claim 1, wherein said immunoassay is an immunomagnetic assay or an immunofluorescent assay.

3. The method of claim 1, wherein said immunoassay utilizes one or more labeled antibodies specific for one or more of CTC, estrogen receptor, HER-2, bcl-2, or ki67.

4. The method of claim 3, wherein said label is a fluorescent label.

5. The method of claim 1, wherein said amplification assay is selected from a multiplex PCR assay, an rt-PCR assay, and a PCR assay.

6. The method of claim 1, wherein said hybridization assay is selected from an in situ hybridization assay and a microarray.

7. The method of claim 1, wherein said aromatase inhibitor is selected from the group consisting of letrozole, anastrozole, and exemestane.

8. The method of claim 1, further comprising the step of detecting an apoptosis marker, wherein said apoptosis marker is detected using monoclonal antibody M30.

9. The method of claim 1, wherein said breast cancer is metastatic.

10. The method of claim 1, wherein said breast cancer is estrogen receptor positive.

11. A method for determining a treatment course of action, comprising
   a) collecting a sample from a subject with breast cancer;
   b) having said sample tested for the level of circulating tumor cells (CTC) in a sample from a subject with breast cancer using staining and an immunoassay and the level of expression of estrogen receptor, HER-2, bcl-2, and ki67 on said CTC using a detection method selected from the group consisting of an immunoassay, nucleic acid amplification, and nucleic acid hybridization;
   c) calculating a numerical CTC-Endocrine Therapy Index (CTC-ETI) based on said number of CTC positive for expression of said estrogen receptor, HER-2, bcl-2, ki67, and total number of CTC, calculating a numerical CTC-Endocrine Therapy Index (CTC-ETI) based on said number of CTC positive for expression of said estrogen receptor, HER-2, bcl-2, ki67, and total number of CTC, wherein said CTC-ETI is calculated by i) assigning zero points when the number of CTC is 0-4 per 7.5 ml, 1 point when the number of CTC is 5-10 per 7.5 ml, and 2 points when the number of CTC is greater than 10 per 7.5 ml; ii) assigning zero points when the number of CTC positive for estrogen receptor is greater than 10%, assigning 2 point when the number of CTC positive for estrogen receptor is 1-10%, and assigning 6 points when the number of CTC positive for estrogen receptor is zero; iii) assigning zero points when the number of CTC positive for HER-2 is 0%, assigning 1 point when the number of CTC positive for HER-2 is 1-10%, and assigning two points when the number of CTC positive for HER-2 is greater than 10%; iv) assigning zero points when the number of CTC positive for bcl-2 is greater than 10%, assigning 1 point when the number of CTC positive for bcl-2 is 1-10%, and assigning 2 points when the number of bcl-2 is 0%; v) assigning zero points when the number of CTC positive for ki67 is 0%, assigning 1 point when the number of CTC positive for Ki-67 is 1-10%, and assigning 2 points when the number of CTC positive for Ki-67 is greater than 10%; and vi) adding said points to obtain said CTC-ETI;
   d) administering an anti-estrogen therapy selected from the group consisting of a selective estrogen receptor modulator (SERM) and an aromatase inhibitor when said CTC-ETI is between 0 and 6 and administering chemotherapy when said CTC-ETI is between 7 and 14.

12. The method of claim 11, wherein said immunoassay is an immunomagnetic assay or an immunofluorescent assay.

13. The method of claim 11, wherein said immunoassay utilizes one or more labeled antibodies specific for one or more of CTC, estrogen receptor, HER-2, bcl-2, or ki67.

14. The method of claim 13, wherein said label is a fluorescent label.

15. The method of claim 11, wherein said aromatase inhibitor is selected from the group consisting of letrozole, anastrozole, and exemestane.

16. The method of claim 1, wherein said step (c) of calculating said CTC-ETI is performed by a computer.

17. The method of claim 11, wherein said step (c) of calculating said CTC-ETI is performed by a computer.

* * * * *

UNITED STATES PATENT AND TRADEMARK OFFICE
CERTIFICATE OF CORRECTION

PATENT NO. : 9,568,476 B2
APPLICATION NO. : 14/304364
DATED : February 14, 2017
INVENTOR(S) : Daniel Hayes It is certified that error appears in the above-identified patent and that said Letters Patent is hereby corrected as shown below:

In the Claims

Column 23 Lines 60-67 and Column 24 Lines 30-67:
Claim 1 reads: "A method for determining a treatment course of action, comprising
a) detecting the level of circulating tumor cells (CTC) in a sample from a subject with breast cancer using staining and an immunoassay;
b) measuring the level of expression of estrogen receptor, HER-2, bcl-2, and ki67 on said CTC using a detection method selected from the group consisting of an immunoassay, nucleic acid amplification, and nucleic acid hybridization;
c) calculating a numerical CTC-Endocrine Therapy Index (CTC-ETI) based on said number of CTC positive for expression of said estrogen receptor, HER-2, bcl-2, ki67, and total number of CTC, wherein said CTC-ETI is calculated by i) assigning zero points when the number of CTC is 0-4 per 7.5 ml, 1 point when the number of CTC is 5-10 per 7.5 ml, and 2 points when the number of CTC is greater than 10 per 7.5 ml; ii) assigning zero points when the number of CTC positive for estrogen receptor is greater than 10%, assigning 2 point when the number of CTC positive for estrogen receptor is 1-10%, and assigning 6 points when the number of CTC positive for estrogen receptor is zero; iii) assigning zero points when the number of CTC positive for HER-2 is 0%, assigning 1 point when the number of CTC positive for HER-2 is 1-10%, and assigning two points when the number of CTC positive for HER-2 is greater than 10%; iv) assigning zero points when the number of CTC positive for bcl-2 is greater than 10%, assigning 1 point when the number of CTC positive for bcl-2 is 1-10%, and assigning 2 points when the number of bcl-2 is 0%; v) assigning zero points when the number of CTC positive for ki67 is 0%, assigning 1 point when the number of CTC positive for Ki-67 is 1-10%, and assigning 2 points when the number of CTC positive for Ki-67 is greater than 10%; and vi) adding said points to obtain said CTC-ETI; and
d) administering an anti-estrogen therapy selected from the group consisting of a selective estrogen receptor modulator (SERM) and an aromatase inhibitor when said CTC-ETI is between 0 and 6 and administering chemotherapy when said CTC-ETI is between 7 and 14."

Signed and Sealed this
Fourth Day of July, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,568,476 B2

HOWEVER, IT SHOULD READ:
Claim 1: "A method for determining a treatment course of action, comprising
a) detecting the level of circulating tumor cells (CTC) in a sample from a subject with breast cancer using staining and an immunoassay;
b) measuring the level of expression of estrogen receptor, HER-2, bcl-2, and ki67 on said CTC using a detection method selected from the group consisting of an immunoassay, nucleic acid amplification, and nucleic acid hybridization;
c) calculating a numerical CTC-Endocrine Therapy Index (CTC-ETI) based on said number of CTC positive for expression of said estrogen receptor, HER-2, bcl-2, ki67, and total number of CTC, wherein said CTC-ETI is calculated by i) assigning zero points when the number of CTC is 0-4 per 7.5 ml, 1 point when the number of CTC is 5-10 per 7.5 ml, and 2 points when the number of CTC is greater than 10 per 7.5 ml; ii) assigning zero points when the number of CTC positive for estrogen receptor is greater than 10%, assigning 2 points when the number of CTC positive for estrogen receptor is 1-10%, and assigning 6 points when the number of CTC positive for estrogen receptor is zero; iii) assigning zero points when the number of CTC positive for HER-2 is 0%, assigning 1 point when the number of CTC positive for HER-2 is 1-10%, and assigning two points when the number of CTC positive for HER-2 is greater than 10%; iv) assigning zero points when the number of CTC positive for bcl-2 is greater than 10%, assigning 1 point when the number of CTC positive for bcl-2 is 1-10%, and assigning 2 points when the number of bcl-2 is 0%; v) assigning zero points when the number of CTC positive for ki67 is 0%, assigning 1 point when the number of CTC positive for Ki-67 is 1-10%, and assigning 2 points when the number of CTC positive for Ki-67 is greater than 10%; and vi) adding said points to obtain said CTC-ETI; and
d) administering an anti-estrogen therapy selected from the group consisting of a selective estrogen receptor modulator (SERM) and an aromatase inhibitor when said CTC-ETI is between 0 and 6 and administering chemotherapy when said CTC-ETI is between 7 and 14."

Column 25 Lines 24-44 and Column 26 Lines 1-28:
Claim 11 reads: "A method for determining a treatment course of action, comprising
a) collecting a sample from a subject with breast cancer;
b) having said sample tested for the level of circulating tumor cells (CTC) in a sample from a subject with breast cancer using staining and an immunoassay and the level of expression of estrogen receptor, HER-2, bcl-2, and ki67 on said CTC using a detection method selected from the group consisting of an immunoassay, nucleic acid amplification, and nucleic acid hybridization;
c) calculating a numerical CTC-Endocrine Therapy Index (CTC-ETI) based on said number of CTC positive for expression of said estrogen receptor, HER-2, bcl-2, ki67, and total number of CTC, calculating a numerical CTC-Endocrine Therapy Index (CTC-ETI) based on said number of CTC positive for expression of said estrogen receptor, HER-2, bcl-2, ki67, and total number of CTC, wherein said CTC-ETI is calculated by i) assigning zero points when the number of CTC is 0-4 per 7.5 ml, 1 point when the number of CTC is 5-10 per 7.5 ml, and 2 points when the number of CTC is greater than 10 per 7.5 ml; ii) assigning zero points when the number of CTC positive for estrogen receptor is greater than 10%, assigning 2 point when the number of CTC positive for estrogen receptor is 1-10%, and assigning 6 points when the number of CTC positive for estrogen receptor is zero; iii) assigning zero points when the number of CTC positive for HER-2 is 0%, assigning 1 point when the number of CTC positive for HER-2 is 1-10%, and assigning two points when the number of

CERTIFICATE OF CORRECTION (continued)
U.S. Pat. No. 9,568,476 B2

CTC positive for HER-2 is greater than 10%; iv) assigning zero points when the number of CTC positive for bcl-2 is greater than 10%, assigning 1 point when the number of CTC positive for bcl-2 is 1-10%, and assigning 2 points when the number of bcl-2 is 0%; v) assigning zero points when the number of CTC positive for ki67 is 0%, assigning 1 point when the number of CTC positive for Ki-67 is 1-10%, and assigning 2 points when the number of CTC positive for Ki-67 is greater than 10%; and vi) adding said points to obtain said CTC-ETI;

d) administering an anti-estrogen therapy selected from the group consisting of a selective estrogen receptor modulator (SERM) and an aromatase inhibitor when said CTC-ETI is between 0 and 6 and administering chemotherapy when said CTC-ETI is between 7 and 14."

HOWEVER, IT SHOULD READ:
Claim 11: "A method for determining a treatment course of action, comprising
a) collecting a sample from a subject with breast cancer;
b) having said sample tested for the level of circulating tumor cells (CTC) in a sample from a subject with breast cancer using staining and an immunoassay and the level of expression of estrogen receptor, HER-2, bcl-2, and ki67 on said CTC using a detection method selected from the group consisting of an immunoassay, nucleic acid amplification, and nucleic acid hybridization;
c) calculating a numerical CTC-Endocrine Therapy Index (CTC-ETI) based on said number of CTC positive for expression of said estrogen receptor, HER-2, bcl-2, ki67, and total number of CTC, wherein said CTC-ETI is calculated by i) assigning zero points when the number of CTC is 0-4 per 7.5 ml, 1 point when the number of CTC is 5-10 per 7.5 ml, and 2 points when the number of CTC is greater than 10 per 7.5 ml; ii) assigning zero points when the number of CTC positive for estrogen receptor is greater than 10%, assigning 2 points when the number of CTC positive for estrogen receptor is 1-10%, and assigning 6 points when the number of CTC positive for estrogen receptor is zero; iii) assigning zero points when the number of CTC positive for HER-2 is 0%, assigning 1 point when the number of CTC positive for HER-2 is 1-10%, and assigning two points when the number of CTC positive for HER-2 is greater than 10%; iv) assigning zero points when the number of CTC positive for bcl-2 is greater than 10%, assigning 1 point when the number of CTC positive for bcl-2 is 1-10%, and assigning 2 points when the number of bcl-2 is 0%; v) assigning zero points when the number of CTC positive for ki67 is 0%, assigning 1 point when the number of CTC positive for Ki-67 is 1-10%, and assigning 2 points when the number of CTC positive for Ki-67 is greater than 10%; and vi) adding said points to obtain said CTC-ETI;
d) administering an anti-estrogen therapy selected from the group consisting of a selective estrogen receptor modulator (SERM) and an aromatase inhibitor when said CTC-ETI is between 0 and 6 and administering chemotherapy when said CTC-ETI is between 7 and 14."